US005364003A

United States Patent [19]

Williamson, IV

[11] Patent Number: 5,364,003

[45] Date of Patent: Nov. 15, 1994

[54] STAPLE CARTRIDGE FOR A SURGICAL STAPLER

[75] Inventor: Warren P. Williamson, IV, Loveland, Ohio

[73] Assignee: Ethicon Endo-Surgery, Cincinnati, Ohio

[21] Appl. No.: 58,393

[22] Filed: May 5, 1993

[51] Int. Cl.[5] .......... A61B 17/068

[52] U.S. Cl. .......... 227/178; 227/19; 227/180

[58] Field of Search .......... 227/19, 175, 178, 179, 227/180

[56] References Cited

U.S. PATENT DOCUMENTS

| | | | |
|---|---|---|---|
| 3,079,606 | 3/1963 | Bobrov et al. . | |
| 3,490,675 | 1/1970 | Green et al. . | |
| 3,499,591 | 3/1970 | Green . | |
| 4,305,539 | 12/1981 | Korolkov et al. . | |
| 4,605,001 | 8/1986 | Rothfuss et al. | 227/178 |
| 4,633,861 | 1/1987 | Chow et al. | 227/180 |
| 4,633,874 | 1/1987 | Chow et al. . | |
| 4,978,049 | 12/1990 | Green . | |
| 5,129,570 | 7/1992 | Schulze et al. | 227/180 |
| 5,275,323 | 1/1994 | Schulze et al. | 227/180 |

*Primary Examiner*—Scott A. Smith

*Attorney, Agent, or Firm*—Dressler, Goldsmith, Shore & Milnamow, Ltd.

[57] ABSTRACT

A staple cartridge for a surgical stapler includes a staple drive member which is driven by longitudinal movement of a cam through the surgical stapler for firing at least one surgical staple. The staple drive member comprises a staple drive element having a staple driving surface in association with the surgical staple for angular orientation of the surgical staple, when applied, with respect to the direction of movement of the cam. The staple drive member further comprises a cam contact element having a cam contact surface for being engaged by the cam, and an arrangement for pivotally connecting the staple drive element to the cam contact element.

5 Claims, 5 Drawing Sheets

60a
60
58
52
26
54
54
44
38
86
40
78
76
82
68
68
80
72
24
84

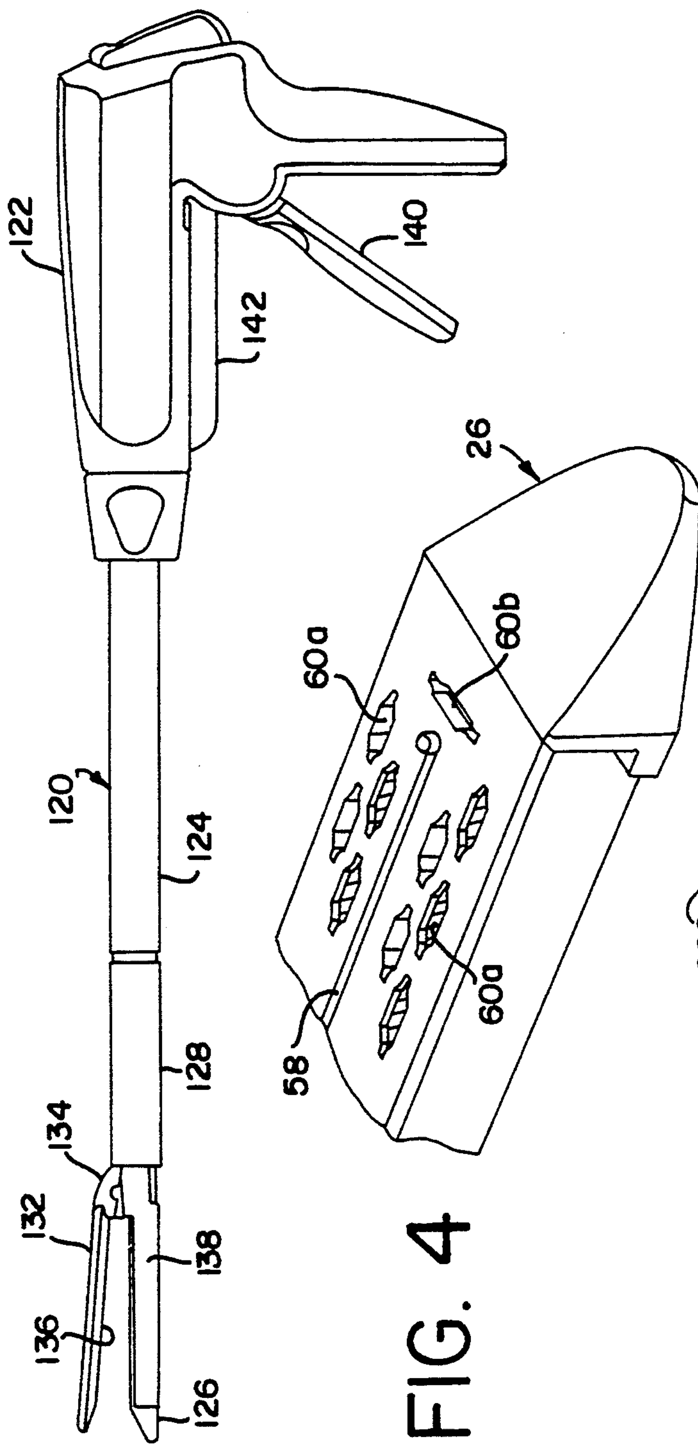
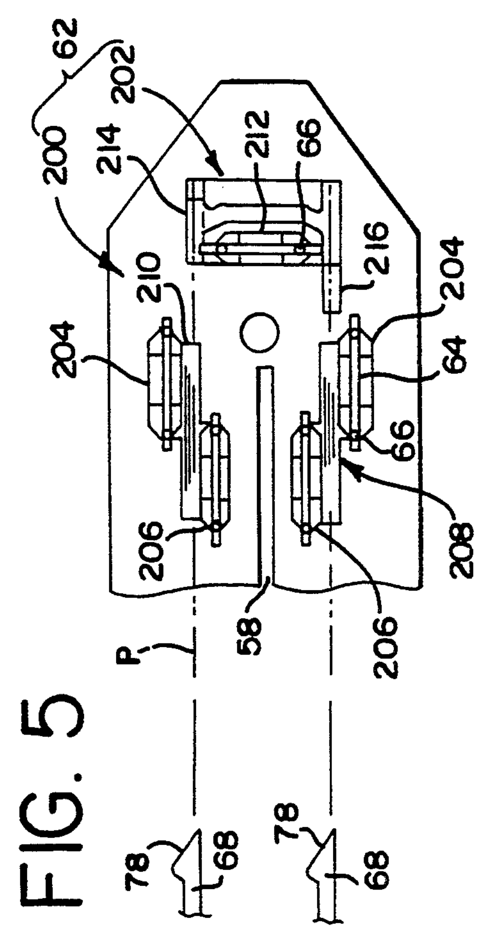
FIG. 6
T M L

FIG. 7
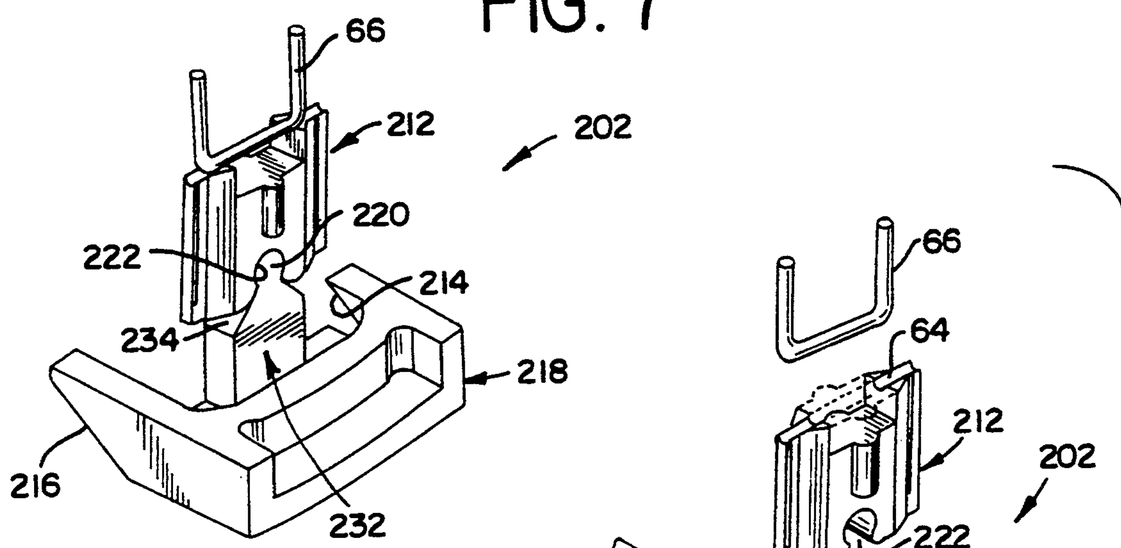
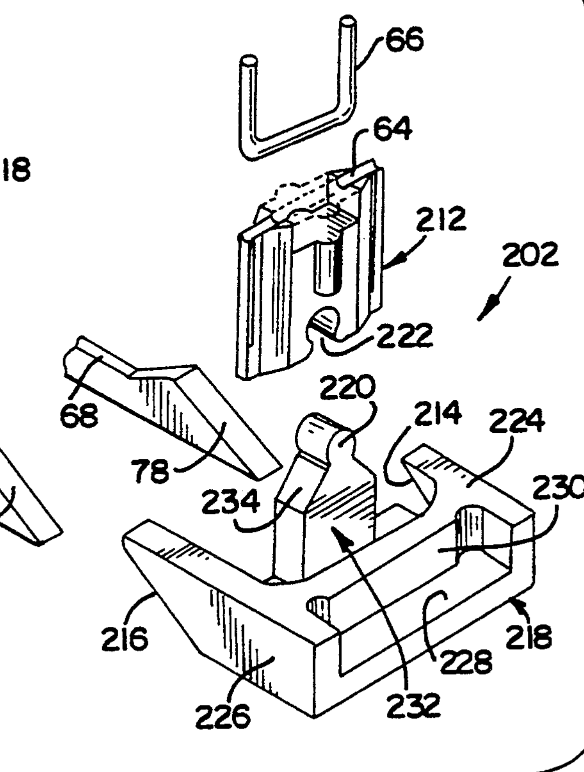
FIG. 8
FIG. 9
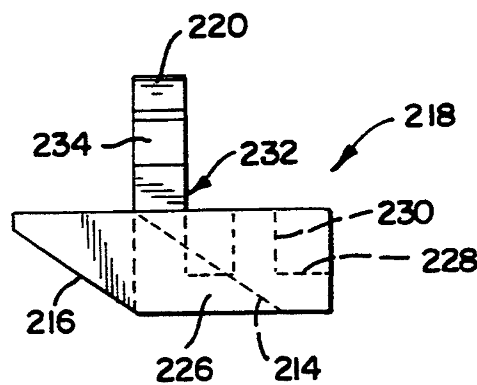
FIG. 10
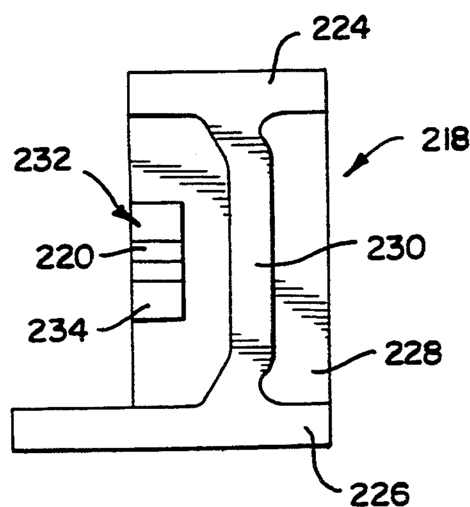

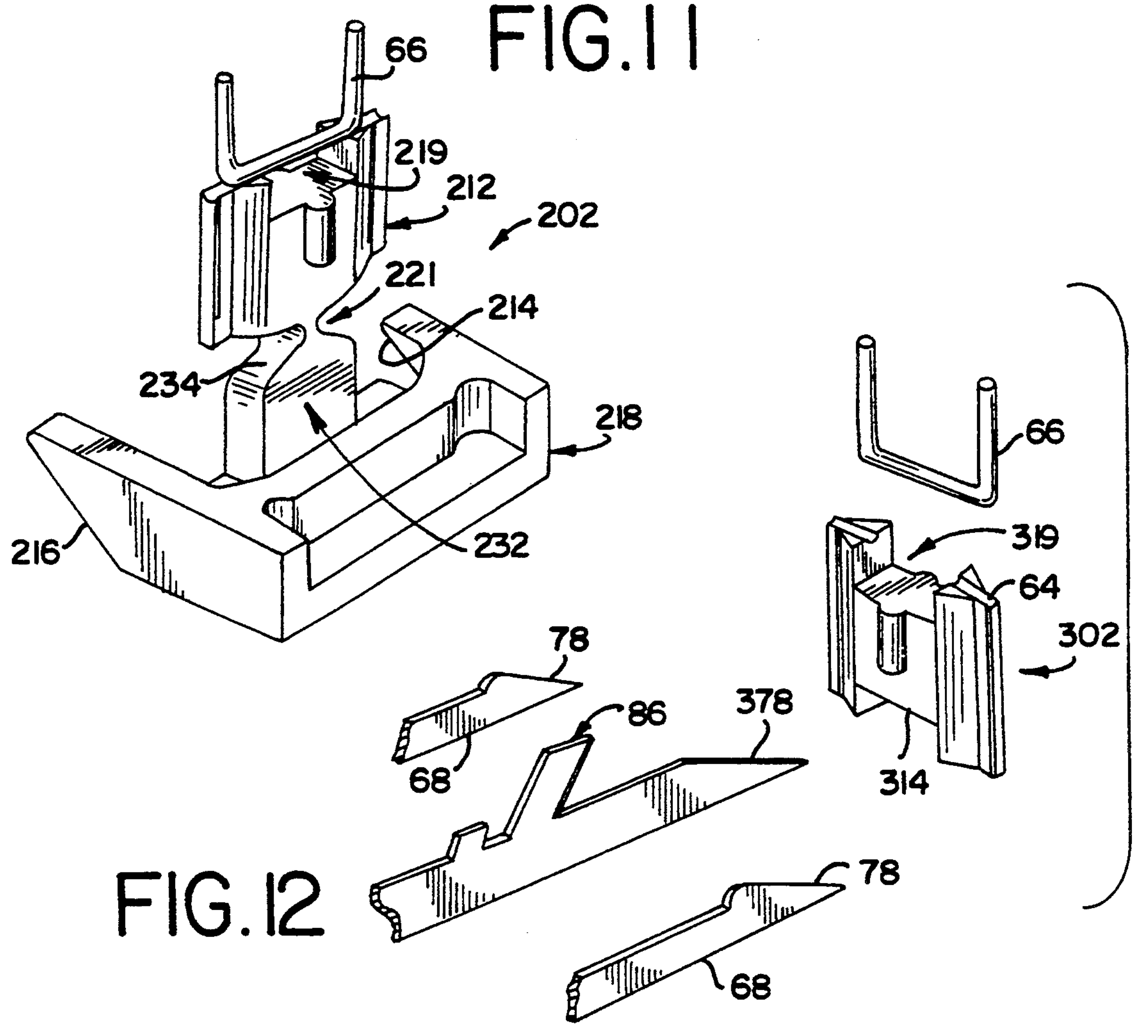
FIG.11
66
219
212
202
221
214
234
218
232
216
66
319
64
302
78
86
378
68
314
FIG.12
78
68
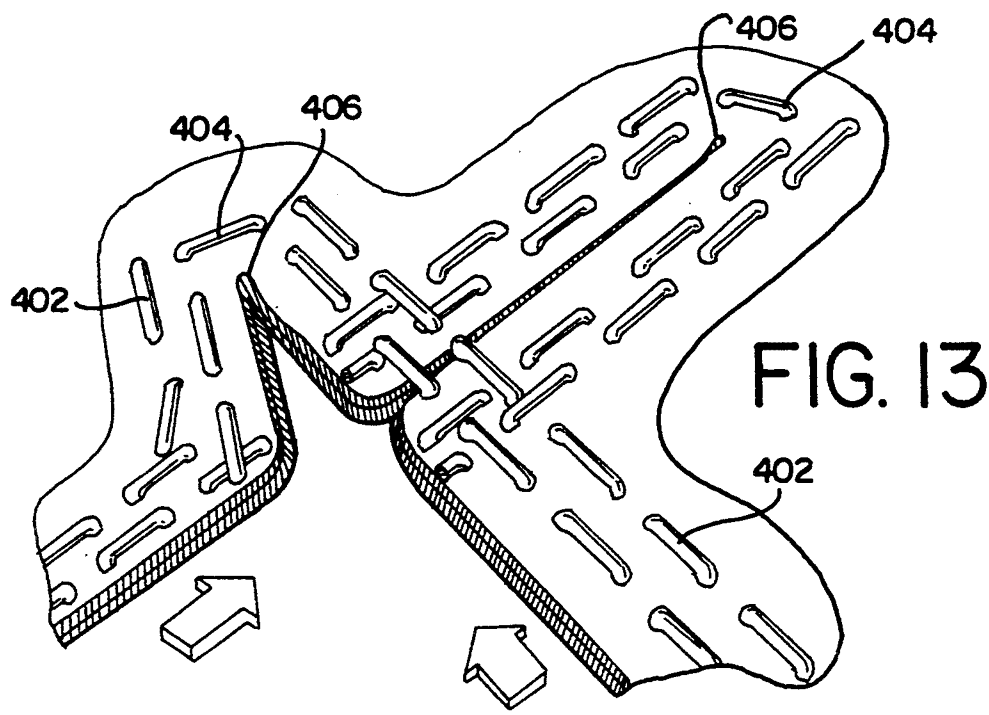
406
404
404
406
402
FIG. 13
402

STAPLE CARTRIDGE FOR A SURGICAL STAPLER

FIELD OF THE INVENTION

The present invention relates to an improved staple cartridge for a surgical stapler of the type which includes a plurality of staple drive members in association with surgical staples which are designed to be driven by longitudinal movement of cam means for firing the surgical staples into body tissue. In particular, the present staple cartridge permits application of staples with a distally disposed staple arranged generally transversely of the remaining staples applied by the device.

BACKGROUND OF THE INVENTION

Surgical staplers have found wide-spread acceptance in surgical procedures since such devices drastically reduce the amount of time required by surgeons to suture body tissue.

Typically, such surgical staplers have a pair of upper and lower jaw members to clamp body tissue therebetween. The lower jaw member carries a staple cartridge which contains a plurality of staple drive members having cam contact surfaces in association with one or more laterally spaced rows of surgical staples. The upper jaw member has an anvil portion to close the surgical staples which have passed through body tissue. The stapler is further provided with at least one pusher bar longitudinally moveable relative to the jaw members and having a cam surface for engaging the cam contact surfaces of the staple drive members, so that the longitudinal movement of the pusher bar sequentially drives the staple drive members, through a camming action, to fire surgical staples from the cartridge.

When the surgical stapler of such typical construction is operated, the surgical staples are driven into the body tissues grasped between the upper and lower jaw members. Sometimes, a simultaneous longitudinal motion of a knife blade follows to cut the tissues along or between the one or more rows of closed surgical staples. As a typical result, at least one longitudinal row of surgical staples is placed on each of the opposite sides of the tissue cutting line to provide hemostasis along the cutting line. However, there remains the possibility of leakage between the tissues at a distal end of the cutting line and consequent bleeding therefrom since a suture is not placed transversely beyond the distal end of the cutting line to tightly hold the tissues.

It is therefore desirable to provide a cartridge having at least one staple drive member capable of placing one or more surgical staples extending beyond the distal end of the tissue cutting line, with such staples arranged generally transversely of the rows of staples formed to provide hemostasis at the distal end of the cutting line.

SUMMARY OF THE INVENTION

The present invention provides a staple cartridge having a specially configured staple drive member for use with a surgical stapler. The staple drive member is designed to be driven by longitudinal movement of a cam through the cartridge of the surgical stapler for firing at least one surgical staple. The staple drive member comprises a staple drive element having a staple driving surface in association with the surgical staple for angular orientation of the surgical staple, when applied, with respect to the direction of movement of the cam. The staple drive member further comprises at least one cam contact element having a cam contact surface for being engaged by the cam. A connecting means is provided to connect the staple drive element to the cam contact element.

In one embodiment of the present invention, the staple driving surface of the cartridge staple drive element is laterally oriented at substantially a right angle to the direction of movement of the cam.

The connecting means may comprise a pivotal projection on one of the cam contact element and the staple drive element, and means for pivotally retaining the pivotal projection on the other of the cam contact element and the staple drive element. Alternatively, the connecting means may comprise a flexible portion of the drive member for integrally connecting the cam contact element and the staple drive element.

The present invention further provides a surgical stapler which comprises cam means comprising a pair of pusher bars, means for actuating the cam means for a longitudinal firing movement of the cam surfaces, and a plurality of staple drive members driven by the longitudinal movement of the cam surfaces. The staple drive members are arranged on respective opposite sides of a longitudinal knife slot. A plurality of surgical staples are respectively associated with the drive members for firing by the longitudinal movement of the cam surfaces, for forming at least one row of staples on each side of the longitudinal knife slot. The surgical stapler further comprises knife means operatively connected to the actuating means for movement along the knife slot for cutting tissue between the rows of surgical staples on each side of the knife slot, and means for applying a staple generally transversely distally of the knife slot.

The means for applying the staple transversely may comprise a staple drive member for applying a staple in an angular orientation relative to the longitudinal movement of the cam surfaces. In one embodiment, the staple drive member is designed to be driven by a cam surface on the knife means. In another embodiment, the staple drive member is driven by the cam surfaces of the pusher bars.

Numerous other advantages and features of the present invention will become readily apparent from the following detailed description, the appended drawings, and the accompanying claims.

BRIEF DESCRIPTION OF THE DRAWINGS

FIG. 3 is a side elevational view of an endoscopic surgical stapler mounting the staple cartridge in accordance with the present invention;

FIG. 4 is a fragmentary perspective view of the staple cartridge;

FIG. 5 is a fragmentary top view of the staple cartridge, with a portion cut away to show the arrangement of the double-staple drive members and the transverse staple drive member mounted in the cartridge;

FIG. 6 is a diagrammatic view illustrating a staple or stitch pattern provided by the stapling operation of the surgical stapler;

FIGS. 7 and 8 are a perspective view and an exploded perspective view of the transverse staple drive member, respectively;

FIGS. 9 and 10, respectively, are a side elevational view and a top view of the cam contact element of the transverse staple drive member;

FIG. 11 is a perspective view of another embodiment of the transverse staple drive member;

FIG. 12 is an exploded perspective view of another embodiment of the transverse staple drive member which is illustrated to be driven by a cam surface on the knife means; and FIG. 13 is another diagrammatic view illustrating a staple or stitch pattern provided by the stapling operation of the surgical stapler wherein transverse staples close off tissue gaps at respective distal ends of two tissue cutting lines.

DETAILED DESCRIPTION

Figure 1:
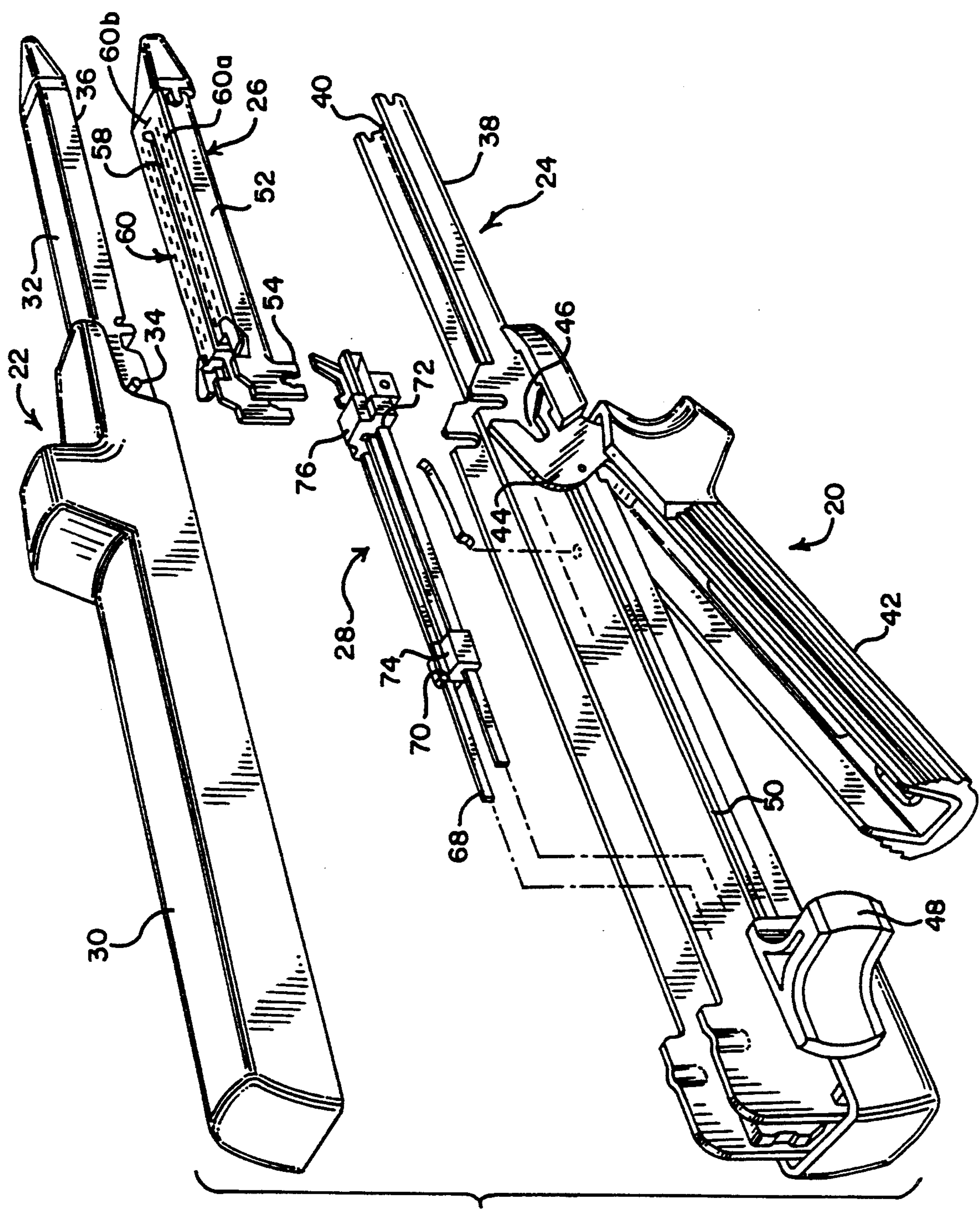
FIG. 1 is an exploded perspective view of a surgical stapler embodying the principles of the present invention.

While the present invention is susceptible of embodiment in various forms, there is shown in the drawings and will hereinafter be described various a presently preferred embodiment of the invention, with the understanding that the present disclosure is to be considered as an exemplification of the invention, and is not intended to limit the invention to the specific embodiments illustrated and described herein.

Figure 2:
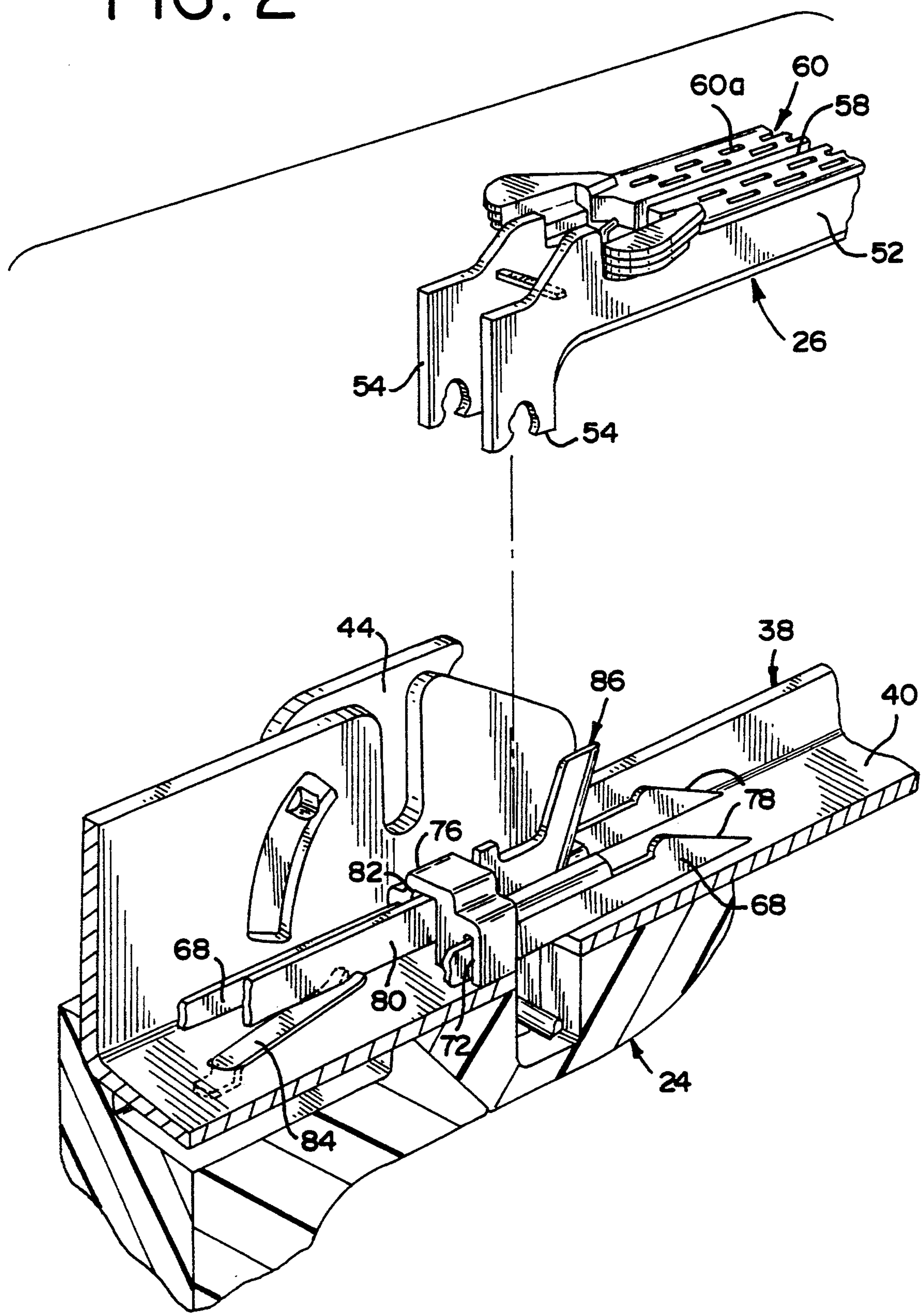
FIG. 2 is an exploded, partly broken away, perspective view of the firing means of the stapler of FIG. 1.

Referring now to the drawings, therein is illustrated in FIGS. 1 and 2, a surgical stapler 20 which generally comprises an upper frame 22, a lower frame 24, a staple cartridge 26 and a firing means 28. An exemplary construction is illustrated in U.S. patent application Ser. No. 07/620,119, filed Nov. 30, 1990, now U.S. Pat. No. 5,129,570, issued Jul. 14, 1992, hereby incorporated by reference.

The upper frame 22 has an upper handle portion 30, an upper jaw portion 32 extending forwardly from the upper handle portion 30, and a latch pin 34 extending outwardly from opposite side faces of the upper jaw portion 32. The upper jaw portion 32 has in its inner surface an anvil portion 36 to close surgical staples which have penetrated through body tissues.

The lower frame 24 supports a lower jaw portion 38 projecting forwardly therefrom. The lower jaw portion 38 has an interior channel 40 into which the staple cartridge 26 is fitted and received.

A pivotal handle 42 is pivotally attached to the lower frame 24 so as to move between a release position and a locking position. The pivotal handle 42 includes a C-shaped hook member 44 having a locking cavity 46 for receiving the latch pin 34. When the pivotal handle 42 is moved to the release position as illustrated in FIG. 1, the hook member 44 is disengaged from the latch pin 34 so that the upper and lower frames 22, 24 may be separated from each other. As the pivotal handle 42 is moved toward the lower frame 24, the locking cavity 46 of the hook member 44 firmly receives the latch pin 34 in the locking position so that the upper and lower frames 22, 24 are locked together.

The lower frame 24 further includes a firing knob 48 movable along a longitudinally-extending guide slot 50 which is formed in a side wall of the lower frame 24.

As best illustrated in FIG. 2, the staple cartridge 26 has a body including opposite side walls 52 configured to be slidably received in the interior channel 40 of the lower jaw portion 38. The staple cartridge 26 further has at its rear end a pair of laterally spaced parallel projection arms 54 respectively extending downwardly from an underface of the staple cartridge 26. The projection arms 54 are designed to be received in an opening (not shown) formed in a bottom wall of the lower jaw portion 38.

The body of the staple cartridge 26 is laterally divided by a longitudinally-elongated center slot 58 which extends from a rear end of the staple cartridge 26 toward a front end thereof. There are disposed a plurality of staple openings 60 defined by the cartridge body along the elongated center slot 58 for mounting a plurality of staple drive members 62 respectively having at least one staple driving surface 64 in association with a surgical staple 66 (FIG. 5). The staple openings 60 may comprise longitudinal staple openings and/or transverse staple openings.

Referring to FIGS. 1 and 2, the firing means 28 comprises a plurality of movable members, such as a pair of laterally spaced parallel pusher bars 68. The pusher bars 68 are designed to be respectively positioned on opposite sides of the elongated center slot 58. Each of the pusher bars 68 has a rear end operatively connected to the firing knob 48 for longitudinal movement therewith, and a front end extending forwardly through guide slots 70, 72 respectively formed in a guide block 76, with the pusher bars 68 joined together for conjoint movement by a knife block 74. The front end of each pusher bar 68 is provided with a wedge-shaped tip which defines an inclined cam surface 78 for engaging the staple drive members 62 as the pusher bars 68 are longitudinally and forwardly moved. In the illustrated embodiment, the inclined cam surface 78 of one of the pair of pusher bars 68 (left in FIG. 2) is positioned forwardly of that of the other (right in FIG. 2) of the pair of pusher bars 68, so that a staggered or delayed camming action by the pair of the pusher bars 68 effects distribution of the amount of force to drive staple drive members 62 disposed on opposite sides of the center slot 58 as the firing knob is manually operated.

The firing means 28 further comprises a knife support bar 80 which has a rear end connected to the knife block 74 and a front end extending forwardly from the knife block 74 in alignment with the elongated center slot 58 of the staple cartridge 26. The knife support bar 80 is slidably received in a central slot 82 formed in the guide block 76 and is supported by a leaf spring 84. An inclined knife blade 86 having a cutting edge is located at the front end of the knife support bar 80.

In operation, the firing knob 48 is manually advanced in order to move the pusher bars 68 in the longitudinal direction along the guide slots 70, 72. As the pusher bars 68 enter the staple cartridge 26, the cam surfaces 78 of the pusher bars 68 engage the staple drive members 62 positioned within the body of the cartridge and transmit vertical or upward motion to the staple drive members 62. This causes the surgical staples 66 to be driven through the body tissues against the anvil portion 36 of the upper jaw portion 32 so that surgical staples 66 are formed in the tissues gripped between the upper and lower jaw portions 32, 38. The simultaneous longitudinal motion of the knife support bar 80 causes the knife blade 86 to follow cutting the tissues between the parallel sets of one or more staple rows.

FIG. 3 illustrates another exemplary surgical stapler for endoscopic application, during which access to a body cavity is usually effected with the aid of a trocar tube (not shown). An exemplary construction is disclosed in U.S. patent application Ser. No. 07/917,636, filed Jul. 20, 1992, now U.S. Pat. No. 5,307,976, hereby incorporated by reference. An endoscopic surgical stapler 120 generally comprises a handle portion 122, a shaft portion 124, a closure sheath 128, an upper jaw portion 132 having an anvil portion 136 and a rear camming surface 134, a lower jaw portion 138, a staple cartridge 126 mounted in the lower jaw portion 138, a closure handle 140 and a firing handle 142.

The staple cartridge 126 is of essentially similar construction as the staple cartridge 26 of the first stapler embodiment shown in FIGS. 1 through 3, and includes a body which mounts a plurality of rows of staple drive members respectively having at least one staple driving surface in association with a surgical staple. Similarly, the endoscopic surgical stapler 120 includes a firing means of essentially similar construction as the firing means 28 of the first stapler embodiment.

The operation of the closure handle 140 advances the closure sheath 128, which in turn cams the rear camming surface 134 of the upper jaw portion 132, so that the upper jaw portion 132 is closed toward the lower jaw portion 138 for grasping the body tissues therebetween. The firing handle 142 is operable to activate pusher bars which transmit a vertical motion to staple drive members so that surgical staples are driven into the body tissues grasped between the upper and lower jaw portions 132, 138.

FIGS. 4 and 5 respectively show a front portion of the staple cartridge 26. In one embodiment as illustrated in FIG. 4, the staple cartridge 26 has two staggered parallel rows of longitudinal staple openings *60a* on each side of the longitudinally-elongated center slot 58. A single transverse staple opening *60b* is disposed longitudinally forwardly and transversely of the center slot 58.

The staple drive members 62 mounted in the staple cartridge 26 are illustrated in FIG. 5, and include double-staple drive members 200 arranged on opposite sides of the center slot 58 and a transverse staple drive member 202 positioned forwardly and transversely of the center slot 58. Each of the double-staple drive members 200 may be of conventional structure, and comprises laterally spaced, longitudinally staggered outer and inner plates 204, 206, respectively configured to be guided by the staggered pair of longitudinal staple openings *60a*. Each of the outer and inner plates 204, 206 defines the longitudinally-extending staple driving surface 64 in association with the surgical staple 66.

Each of the double-staple drive members 200 further comprises a connecting portion 208 for connecting the outer and inner plates 204, 206. The connecting portion 208 includes a lower cam contact surface at 210, positioned opposite the staple driving surface 64 to extend along a path P of the longitudinal movement of the corresponding pusher bar 68.

The transverse staple drive member 202 embodying the present invention includes a staple drive element 212 configured to be guided by the transverse staple opening *60b*. The staple drive element 212 defines a transversely-extending staple driving surface 64 in association with the surgical staple 66. The transverse staple drive member 202 further includes a cam contact surface for being engaged by a cam surface 78, such as a laterally spaced pair of inclined undersurfaces 214, 216, respectively positioned to extend along the path P (see FIG. 5) of the longitudinal movement of the respective pusher bar 68.

With such a construction, as the pusher bars 68 advance in the longitudinal direction P as indicated by arrows in FIG. 5, each cam surface 78 of the pusher bars 68 sequentially engages and drives the double staple drive members 200 so that two parallel sets of the staggered double row staples are sequentially formed or placed in the tissues, followed by the longitudinal movement of the knife blade 86 along the center slot 58 to cut the tissues between the two parallel sets of the double staple rows. As both pusher bars 68 further advance in the longitudinal direction, the cam surfaces 78 thereof finally simultaneously engage the laterally and longitudinally spaced pair of inclined undersurfaces 214, 216 of the transverse staple drive member 202, so that a transversely oriented surgical staple is driven and formed forwardly of, and perpendicularly, to the cutting line provided by the knife blade 86. As illustrated in FIG. 6, the cutting line L is, as a result, surrounded or closed by the two parallel sets of the formed, double staggered row staples M and the formed transverse staple T.

FIGS. 7 and 8 illustrate one embodiment of the transverse staple drive member 202 in accordance with the present invention. The transverse staple drive member 202 comprises a staple drive element 212 and a cam contact element 218 having the laterally spaced pair of inclined undersurfaces 214, 216 for respective engagement by the cam surfaces 78 of the pusher bars 68.

The staple drive element 212 is illustrated to include a relief slot 219 extending downwardly from a top surface thereof for preventing the surgical stapler 66 from being overdriven. However, as shown in a dotted line in FIG. 8, such a relief slot 219 may be optionally omitted to form a continuous staple driving surface 64. The staple drive element 212 and the cam contact element 218 are operatively connected to each other to the extent that the upward or vertical motion is transmitted from the cam contact element 218 to the staple drive element 212, while rotational torque is substantially prevented from being transmitted therebetween. Such connection serves to prevent jamming which could occur if rotational torque (such as resulting from non-simultaneous engagement of the cam surfaces 78) is undesirably transmitted from the contact element 218 to the drive element 212, acting to rotate the staple drive element 212 within the staple opening.

The cam contact element 218 and the staple drive element 212 may be pivotally connected to each other for pivotal movement relative to each other, through a separate pivotal joint or an integral pivotal joint incorporated therein. In the embodiment as illustrated in FIGS. 7 and 8, the separate pivotal joint is employed to pivotally connect the cam contact element 218 and the staple drive element 212. Specifically, the cam contact element 218 includes a pivotal projection 220, and the staple drive element 212 includes at its lower end a projection receiving slot 222 for pivotally receiving the pivotal projection 220 of the cam contact element 218. Alternatively, the cam contact element 218 may include the projection receiving slot 222 for pivotally receiving the pivotal projection 220 provided in the staple drive element 212.

FIGS. 9 and 10 are a side elevational view and a top view of the cam contact element 218, respectively. The cam contact element 218 comprises a laterally spaced pair of side plates 224, 226 respectively having longitudinally extending inclined undersurfaces 214, 216 for defining the cam contact surfaces. The inclined undersurfaces 214, 216 are staggered in the longitudinal direction so that they are engaged by cam contact surfaces 78 of the pair of the pusher bars 68 at the same time. The cam contact element 218 further comprises a flat base plate 228 for connecting respective lower ends of the pair of side plates 224, 226, a cross member 230 extending between the pair of side plates 224, 226 on the flat base plate 228, so as to define a top surface coterminous with those of the pair of side plates 224, 226, and an upright projection 232 disposed rearwardly of the cross member 230 and extending upwardly from the flat base plate 228 so as to define a rear surface coterminous with that of the flat base plate 228.

The upright projection 232 includes a distal end to define the pivotal projection 220 having a semi-circular cross section, and tapered side surfaces 234 respectively diverging downwardly from the pivotal projection 220 for defining spaces to permit the pivotal movement of the staple drive element 212 about the pivotal projection 220. Such pivotal movement is accommodated to prevent jamming of the drive member 202 in the event that the pusher bars 68 do not simultaneously engage the surfaces 214, 216.

FIG. 11 illustrates another embodiment of the transverse staple drive member 202 which incorporates the integral pivotal joint therein. The transverse staple drive member 202 includes a flexible portion 221 for integrally connecting the cam contact element 218 and the staple drive element 212. Such an integral pivotal joint may be provided in the form of a relatively thin, flexible so-called living hinge.

FIG. 12 illustrates another embodiment of a transverse staple drive member 302 in accordance with the present invention. The transverse staple drive member 302 is configured to be guided by the transverse staple opening **60*b* formed in the cartridge body 26. The transverse staple drive member 302 generally includes the transversely-extending staple driving surface 64 in association with the surgical staple 66, and a relief slot 319. The transverse staple drive member 302 further includes an inclined undersurface 314 for engagement by a cam surface 378 on a distal end of the knife support bar 80**.

FIG. 13 illustrates another diagrammatic view of the stitch pattern provided by the stapling operation of the present surgical stapler. Two consecutive stapling operations in crossing directions as indicated by arrows in FIG. 11, create two intersecting tissue cutting lines. Each cutting line is laterally surrounded or closed by the two parallel sets of the double staggered row staples 402. A transverse staple 404 is placed transversely beyond a distal end 406 of each tissue cutting line so as to longitudinally surround or close the tissue cutting line.

From the foregoing, it will be observed that numerous modifications and variations can be effected without departing from the true spirit and scope of the novel concept of the present invention. It is to be understood that no limitation with respect to the specific embodiment illustrated herein is intended or should be inferred. The disclosure is intended to cover by the appended claims all such modifications as fall within the scope of the claims.

What is claimed is:

1. A surgical stapler comprising:

cam means comprising a pair of pusher bars each having a cam surface;

means for actuating said cam means for a longitudinal firing movement of said cam surfaces;

a plurality of staple drive members driven by the longitudinal movement of said cam surfaces, said staple drive members being arranged on respective opposite sides of a longitudinal knife slot;

a plurality of surgical staples respectively associated with said drive members for being fired by the longitudinal movement of said cam surfaces, for forming at least one row of staples on each side of said slot;

knife means operatively connected to said actuating means for movement along said knife slot for cutting tissue between said rows of staples on opposite sides of said slot, and means for applying a staple generally transversely and distally of said knife slot.

2. A surgical stapler in accordance with claim 1, wherein said means for applying said staple transversely comprises a staple drive member for applying a staple in an angular orientation relative to the longitudinal movement of said cam surfaces.

3. A surgical stapler in accordance with claim 2, wherein said staple drive member is driven by a cam surface on said knife means.

4. A surgical stapler in accordance with claim 2, wherein said staple drive member is driven by the cam surfaces of said pusher bars.

5. A staple cartridge for a surgical stapler having at least one cam longitudinally moveable through said stapler and said cartridge for firing at least one surgical staple, said staple cartridge comprising:

a cartridge body;

a knife slot longitudinally extending in said cartridge body for guiding a knife for cutting tissue;

a transverse staple opening in said cartridge body, said staple opening being disposed distally and transversely of said knife slot; and a staple drive member supported in said transverse staple opening and driven by the longitudinal movement of said cam for firing a surgical staple therethrough, said cartridge further including a plurality of staple openings arranged on respective opposite sides of said knife slot, a plurality of staple drive members respectively supported in said staple openings for driving surgical staples placed thereon.

* * * * *